US012788864B2

(12) United States Patent
Zhang

(10) Patent No.: US 12,788,864 B2
(45) Date of Patent: Nov. 10, 2026

(54) NASAL IRRIGATOR

(71) Applicant: Shenzhen Weierda Plastic Hardware Products Co., Ltd., Shenzhen (CN)

(72) Inventor: Xiandai Zhang, Shenzhen (CN)

(73) Assignee: Shenzhen Weierda Plastic Hardware Products Co., Ltd., Shenzhen (CN)

( * ) Notice: Subject to any disclaimer, the term of this patent is extended or adjusted under 35 U.S.C. 154(b) by 633 days.

(21) Appl. No.: 18/229,188

(22) Filed: Aug. 2, 2023

(65) Prior Publication Data

US 2024/0115796 A1 Apr. 11, 2024

(30) Foreign Application Priority Data

Oct. 8, 2022 (CN) ........................ 202211230657.8

(51) Int. Cl.
*A61M 3/02* (2006.01)

(52) U.S. Cl.
CPC ........ *A61M 3/0229* (2013.01); *A61M 3/0202* (2021.05); *A61M 3/0258* (2013.01); *A61M 3/0279* (2013.01); *A61M 2205/13* (2013.01); *A61M 2205/14* (2013.01); *A61M 2205/3584* (2013.01); *A61M 2210/0618* (2013.01)

(58) Field of Classification Search
CPC .............. A61M 3/0258; A61M 3/0283; A61M 3/0201; A61M 3/0279; A61M 3/02; A61M 1/77; A61M 1/72; A61M 1/774; A61M 2005/1416; A61M 5/1418; A61M 5/14244; A61M 39/24; A61M 2205/13; A61M 2205/14; A61M 2205/3584; A61M 2210/0618; F24F 2006/146; F24F 2006/008; B65D 33/00; A47L 9/2873
See application file for complete search history.

(56) References Cited

U.S. PATENT DOCUMENTS

| | | | | |
|---|---|---|---|---|
| 4,558,484 A * | 12/1985 | Groth | A47L 11/4083 15/353 |
| 4,758,224 A * | 7/1988 | Siposs | F16K 15/147 604/129 |
| 2008/0221507 A1* | 9/2008 | Hoke | A61H 35/04 604/35 |
| 2010/0152653 A1* | 6/2010 | Hoke | A61M 3/0201 604/94.01 |

(Continued)

FOREIGN PATENT DOCUMENTS

WO 2019093843 A1 5/2019

*Primary Examiner* — Michael J Tsai
*Assistant Examiner* — Justin L Zamory
(74) *Attorney, Agent, or Firm* — Bayramoglu Law Offices LLC

(57) ABSTRACT

A nasal irrigator includes a nasal irrigator body, a nasal irrigator handle, a clean water tank, and a dirty water tank. The clean water tank and the dirty water tank are both arranged on a side of the nasal irrigator body, and a water inlet pump communicated with the clean water tank and a dirty water pump communicated with the dirty water tank are provided inside the nasal irrigator body. The nasal irrigator body is provided with an insertion hole configured to fix the nasal irrigator handle, and the nasal irrigator handle is capable of being inserted into the insertion hole or taken out of the insertion hole. A water inlet soft rubber nozzle and a water return soft rubber nozzle are mounted on the nasal irrigator handle.

16 Claims, 14 Drawing Sheets

(56) References Cited

U.S. PATENT DOCUMENTS

| | | | | |
|---|---|---|---|---|
| 2017/0119939 | A1* | 5/2017 | Doerr .................. | A61M 3/0208 |
| 2018/0036201 | A1 | 2/2018 | Hoke et al. | |
| 2019/0336757 | A1* | 11/2019 | Rodriguez ........... | A61N 1/0412 |
| 2022/0323096 | A1* | 10/2022 | Naglreiter .............. | A61B 17/22 |

* cited by examiner

NASAL IRRIGATOR

CROSS REFERENCE TO THE RELATED APPLICATIONS

This application is based upon and claims priority to Chinese Patent Application No. 202211230657.8, filed on Oct. 8, 2022, the entire contents of which are incorporated herein by reference.

TECHNICAL FIELD

The present disclosure relates to the technical field of nasal irrigation devices, and in particular, to a nasal irrigator.

BACKGROUND

A nasal irrigator is used to clean the nasal cavity. It usually employs a certain pressure (such as an airbag type nasal irrigator, gravity such as a simple bottle-can type, or mechanical pressure such as electric type) to send a cleaning liquid (such as saline) into nostrils, which is beneficial for the cleaning liquid to clean the nostrils. Through the above path, with the help of the bactericidal effect of the saline itself and the impact of water flow, accumulated pathogens and pollutants in the nasal cavity are discharged. In this way, a normal physiological environment of the nasal cavity is restored, a self-detoxification function of the nasal cavity is restored, and the purpose of protecting the nasal cavity is achieved.

According to the nasal irrigator in the prior art, dirty water after nasal flushing cannot be recycled, such that the nasal irrigator can only be used in places where there are washstands that can receive wastewater, so use scenarios of the nasal irrigator are limited. The dirty water after flushing also pollutes the flushing places such as the washstands, and a user also needs to clean up the dirty water, causing poor use experience.

SUMMARY

An objective of the present disclosure is to overcome the foregoing defects and provide a nasal irrigator. The nasal irrigator can clean a nasal cavity and recycle dirty water after cleaning, thereby expanding usage scenarios of the nasal irrigator.

The technical solutions of the present disclosure are implemented as follows: the nasal irrigator includes a nasal irrigator body, a nasal irrigator handle, a clean water tank, and a dirty water tank, where

- the clean water tank and the dirty water tank are both arranged on a side of the nasal irrigator body, and a water inlet pump communicated with the clean water tank and a dirty water pump communicated with the dirty water tank are provided inside the nasal irrigator body;
- the nasal irrigator body is provided with an insertion hole configured to fix the nasal irrigator handle, and the nasal irrigator handle is capable of being inserted into the insertion hole or taken out of the insertion hole; and a water inlet soft rubber nozzle and a water return soft rubber nozzle are mounted on the nasal irrigator handle, the water inlet soft rubber nozzle is communicated with the water inlet pump, and the water return soft rubber nozzle is communicated with the dirty water pump.

In the foregoing structure, the nasal irrigator handle includes an upper handle cover and a lower handle cover buckled with each other, and a tail end of the water inlet soft rubber nozzle and a tail end of the water return soft rubber nozzle are fixedly clamped between the upper handle cover and the lower handle cover.

In the foregoing structure, a control printed circuit board (PCB) is provided between the upper handle cover and the lower handle cover, and a control button is provided on the upper handle cover, and configured to implement control over the water inlet pump and the dirty water pump.

In the foregoing structure, a handle cover is provided at the insertion hole of the nasal irrigator body, and the nasal irrigator handle is inserted into the handle cover; and

- a guide plate is fixedly arranged on a side of the handle cover and is located between the handle cover and the water inlet pump and the dirty water pump arranged side by side.

In the foregoing structure, a first water inlet pipe is connected to the water inlet soft rubber nozzle, and the water inlet soft rubber nozzle is communicated with the water inlet pump through the first water inlet pipe; and a first water outlet pipe is connected to the water return soft rubber nozzle, and the water return soft rubber nozzle is communicated with the dirty water pump through the first water outlet pipe.

In the foregoing structure, a second water inlet pipe is connected to the clean water tank, and the clean water tank is communicated with the water inlet pump through the second water inlet pipe; and a second water outlet pipe is connected to the dirty water tank, and the dirty water tank is communicated with the dirty water pump through the second water outlet pipe.

In the foregoing structure, a fixed frame is fixedly arranged in the nasal irrigator body, a limiting hole is formed in the fixed frame in a penetrating manner, and the first water inlet pipe and the first water outlet pipe pass through the limiting hole.

In the foregoing structure, the water inlet pump and the dirty water pump are fixed in a water pump silicone case, a body cover is provided on a side of the water pump silicone case and has an accommodating cavity with an open upper end, and a drooping part of the first water inlet pipe and a drooping part of the first water outlet pipe are located in the accommodating cavity of the body cover.

In the foregoing structure, a tee joint is provided at a middle of the first water inlet pipe, communication of the first water inlet pipe is implemented by two ends of the tee joint, a vent pipe is connected to another port of the tee joint, and an air one-way valve is provided at a tail end of the vent pipe and allows injection of air into the first water inlet pipe.

In the foregoing structure, the clean water tank includes an upper clean water tank cover and a lower clean water tank cover buckled with the upper clean water tank cover, and the lower clean water tank cover is provided with a first accommodating cavity configured to accommodate clean water.

In the foregoing structure, the upper clean water tank cover is provided with a second accommodating cavity configured to accommodate a saline pack, a through hole communicated with the first accommodating cavity is formed in a bottom surface of the second accommodating cavity, and spikes configured to puncture the saline pack are provided on a periphery of the through hole.

In the foregoing structure, a pressing plate of the upper clean water tank cover and a clean water tank clamshell cover are provided in the second accommodating cavity, the clean water tank clamshell cover is rotatably connected to the upper clean water tank cover, a clean water tank button is further provided on the upper clean water tank cover, and the clean water tank clamshell cover is open or closed through the clean water tank button.

In the foregoing structure, a magnetic element configured to sense whether the saline pack is placed in is further provided in the second accommodating cavity of the clean water tank cover.

In the foregoing structure, a notch recessed inward is formed in a side of the nasal irrigator body, and the clean water tank and the dirty water tank are arranged side by side along a vertical direction and then are disposed in the notch of the nasal irrigator body.

In the foregoing structure, a top cover is provided at a top of the nasal irrigator body, a bottom cover is provided at a bottom of the nasal irrigator body, and a battery box configured to accommodate a battery is provided on the bottom cover.

In the foregoing structure, a control PCB is provided inside the nasal irrigator body, a control circuit is integrated on the control PCB, and the control circuit includes a power supply circuit, a data processing circuit, a water pump control circuit, a bluetooth chip circuit, and a touch detection circuit, where

- the power supply circuit is configured to provide electric energy to other circuits;
- the water pump control circuit, the bluetooth chip circuit, and the touch detection circuit are all electrically connected to the data processing circuit and are all controlled by the data processing circuit, and the water pump control circuit is configured to control the water inlet pump and the dirty water pump.

In the foregoing structure, the control circuit further includes an antenna circuit electrically connected to the data processing circuit and the touch detection circuit.

In the foregoing structure, the power supply circuit includes a first power supply circuit configured to provide a voltage of direct current 5 V, and a second power supply circuit configured to provide a voltage of direct current 3.3 V.

The present disclosure has the following beneficial effects: when the nasal irrigator is in use, the water inlet soft rubber nozzle and the water return soft rubber nozzle are respectively aligned with nostrils, and under a driving force of the water inlet pump, the water in the clean water tank is sprayed from the water inlet soft rubber nozzle to clean a nasal cavity. Meanwhile, under a driving force of the dirty water pump, the water return soft rubber nozzle suctions wastewater from another nasal cavity, and the dirty water is stored in the dirty water tank. The cleaning of the nasal cavity is completed in such a way, and the dirty water is recycled after cleaning, thereby expanding usage scenarios of the nasal irrigator. A user has no need to clean the dirty water, thereby improving use experience of the user.

DETAILED DESCRIPTION OF THE EMBODIMENTS

To make the objectives, technical solutions, and advantages of the present disclosure clearer, the present invention is further described below in detail with reference to the drawings and embodiments. It should be understood that the described specific embodiments are merely used to explain the present disclosure, rather than to limit the present disclosure.

Figure 3:
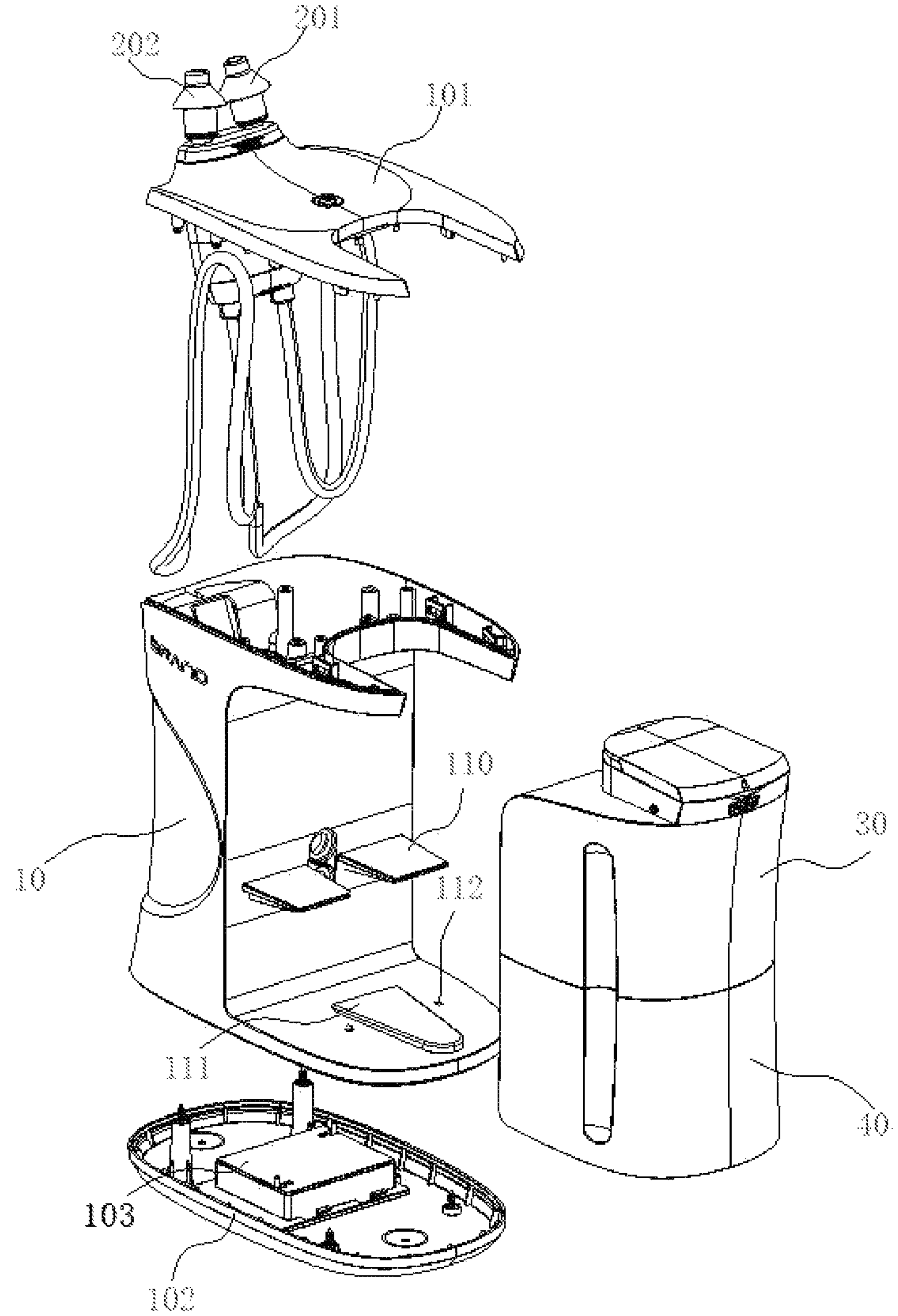
FIG. 3 is an exploded schematic diagram of a nasal irrigator according to the present disclosure.

Referring to FIG. 1 to FIG. 10, the present disclosure discloses a nasal irrigator, which can clean a nasal cavity of a human body. Specifically, the nasal irrigator includes nasal irrigator body 10, nasal irrigator handle 20, clean water tank 30, and dirty water tank 40. The nasal irrigator body 10, the clean water tank 30, and the dirty water tank 40 constitute a structure shown in FIG. 2. The clean water tank 30 and the dirty water tank 40 are both arranged on a side of the nasal irrigator body 10. In this embodiment, as shown in FIG. 3, a notch recessed inward is formed in a side of the nasal irrigator body 10, and the clean water tank 30 and the dirty water tank 40 are arranged side by side along a vertical direction and then are disposed in the notch of the nasal irrigator body 10. In this embodiment, fixed boss 110 is provided on a side wall of the notch of the nasal irrigator body 10 and is configured to carry the clean water tank 30. Protruding portion 111 is provided on a bottom surface of the notch of the nasal irrigator body 10, and correspondingly, a recess portion matched with the protruding portion 111 is provided at a bottom of the dirty water tank 40. Through cooperation between the protruding portion 111 and the recess portion, positioning and mounting of the dirty water tank are facilitated, and the dirty water tank 40 is prevented from being separated from the nasal irrigator body 10 in use. In addition, fixed convex points 112 are respectively provided on two sides of the protruding portion 111, and also achieve a positioning effect. Top cover 101 is provided at a top of the nasal irrigator body 10, bottom cover 102 is mounted at a bottom of the nasal irrigator body 10, and battery box 103 configured to accommodate a battery is provided on the bottom cover 102. The top cover 101 and the nasal irrigator body 10 as well as the bottom cover 102 and the nasal irrigator body 10 are both in buckled connection. However, it should be explained that the present disclosure is not limited to this connection mode. In another embodiment, the top cover 101 and the nasal irrigator body 10 as well as the bottom cover 102 and the nasal irrigator body 10 are both connected through screws.

Figure 1:
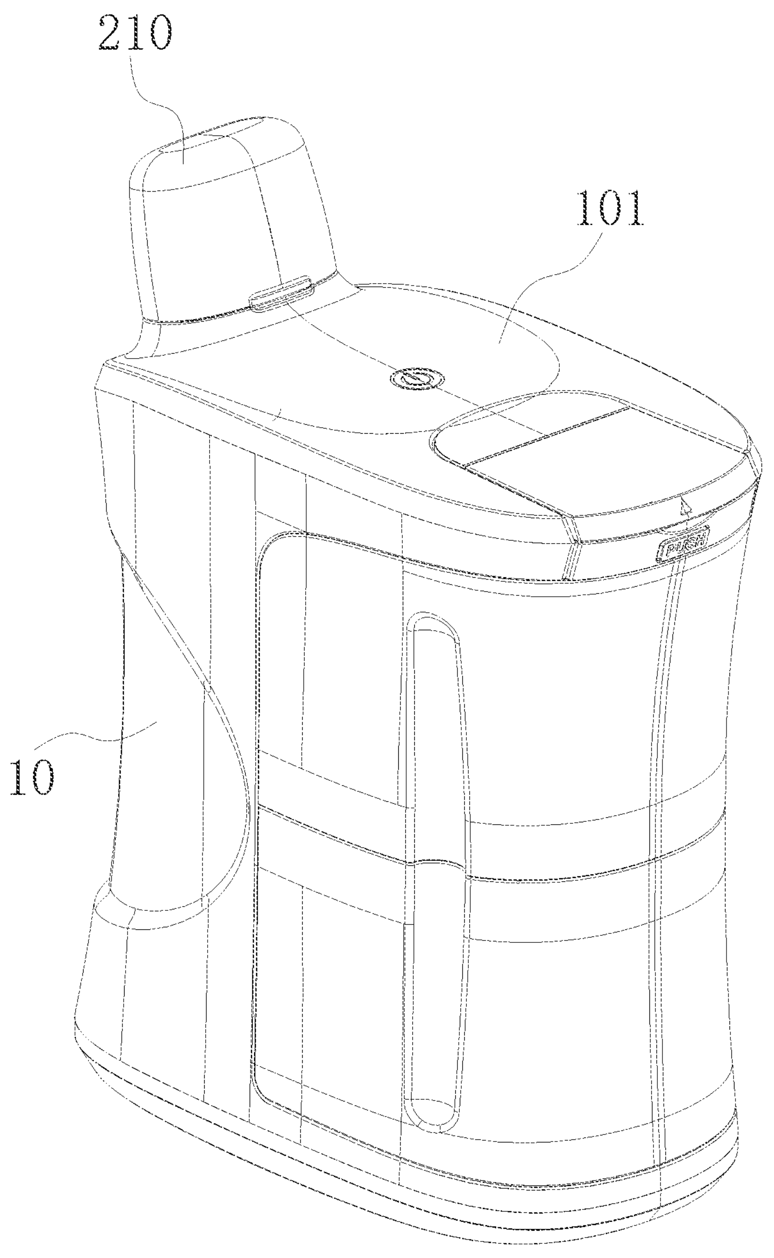
FIG. 1 is a schematic diagram of an overall structure of a nasal irrigator according to the present disclosure.
Figure 2:
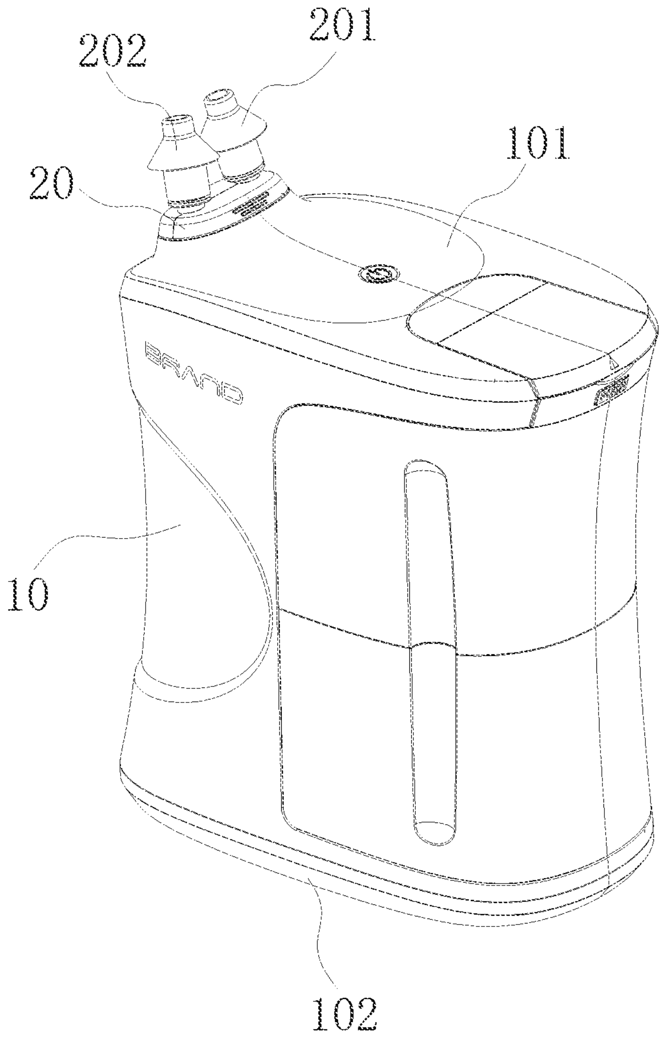
FIG. 2 is a stereoscopic diagram of a partial structure of a nasal irrigator according to the present disclosure.
Figure 6:
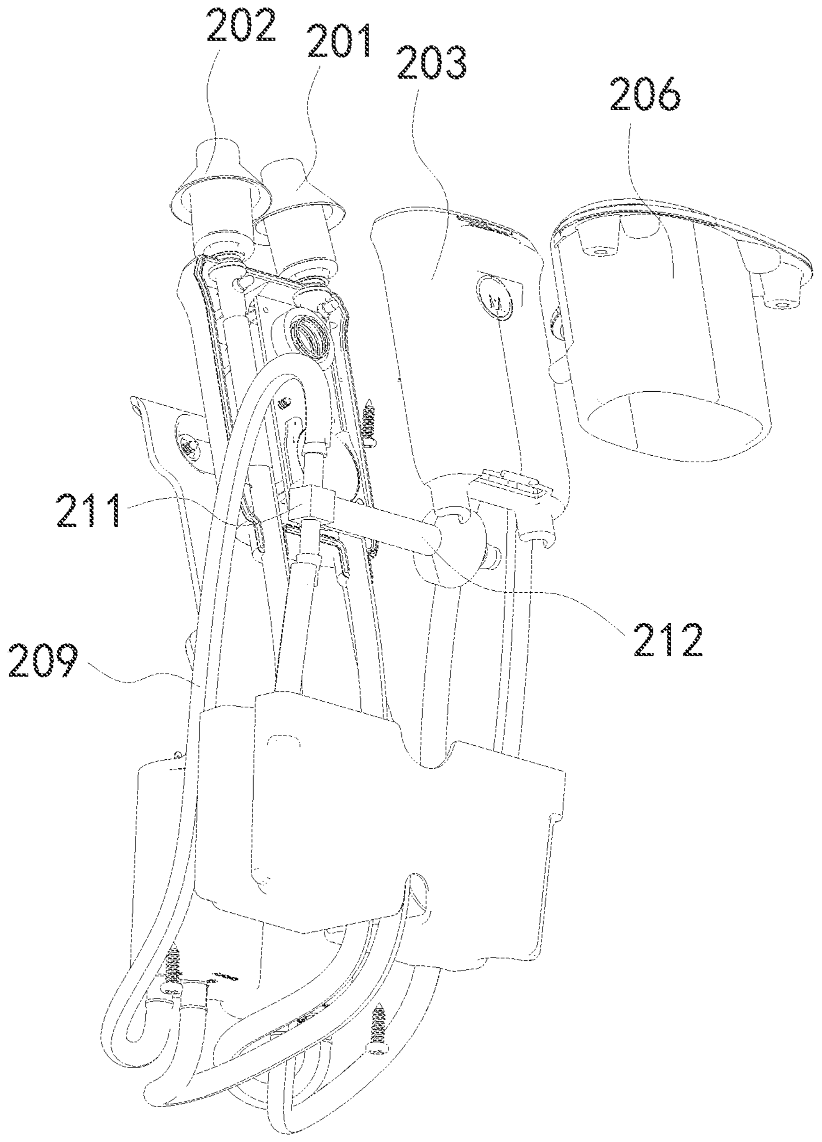
Figure 7:
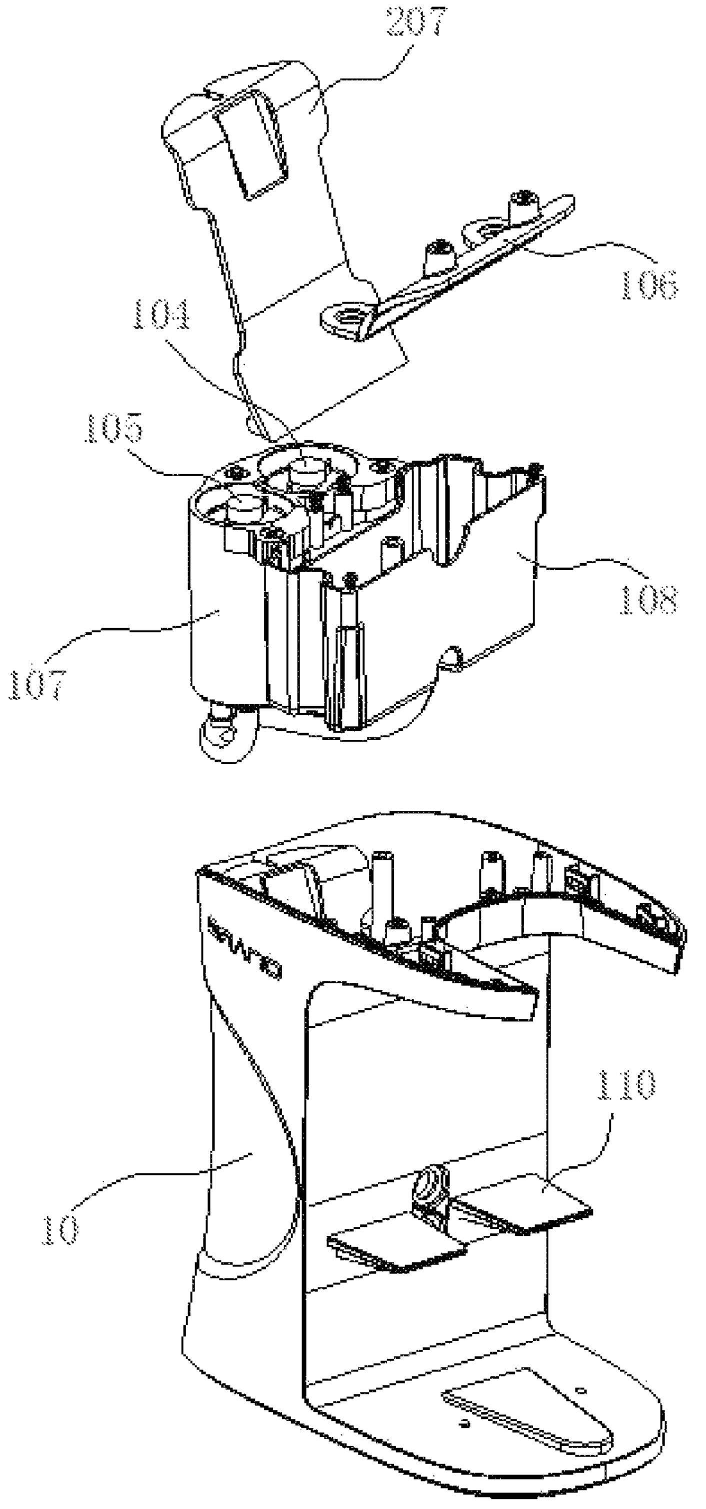
FIG. 7 is an exploded schematic diagram of a nasal irrigator body according to the present disclosure.

As shown in FIG. 6 and FIG. 7, water inlet pump 104 communicated with the clean water tank 30 and dirty water pump 105 communicated with the dirty water tank 40 are provided inside the nasal irrigator body 10. The nasal irrigator body 10 is provided with an insertion hole configured to fix the nasal irrigator handle 20, and the nasal irrigator handle 20 is capable of being inserted into the insertion hole or taken out of the insertion hole. Water inlet soft rubber nozzle 201 and water return soft rubber nozzle 202 are mounted on the nasal irrigator handle 20, the water inlet soft rubber nozzle 201 is communicated with the water inlet pump 104, and the water return soft rubber nozzle 202 is communicated with the dirty water pump 105. As shown in FIG. 1, dustproof cover 210 covers the nasal irrigator handle 20, and achieves a dustproof effect on the nasal irrigator handle when the nasal irrigator is not in use.

Through such a structure, when the nasal irrigator of the present disclosure is in use, the water inlet soft rubber nozzle 201 and the water return soft rubber nozzle 202 are respectively aligned with nostrils, and under a driving force of the water inlet pump 104, the water in the clean water tank 30 is sprayed from the water inlet soft rubber nozzle 201 to clean a nasal cavity. Meanwhile, under a driving force of the dirty water pump 105, the water return soft rubber nozzle 202 suctions wastewater from another nasal cavity, and the dirty water is stored in the dirty water tank 40. The cleaning of the nasal cavity is completed in such a way, and the dirty water is recycled after cleaning, thereby expanding usage scenarios of the nasal irrigator. A user has no need to clean the dirty water, thereby improving use experience of the user.

Figure 4:
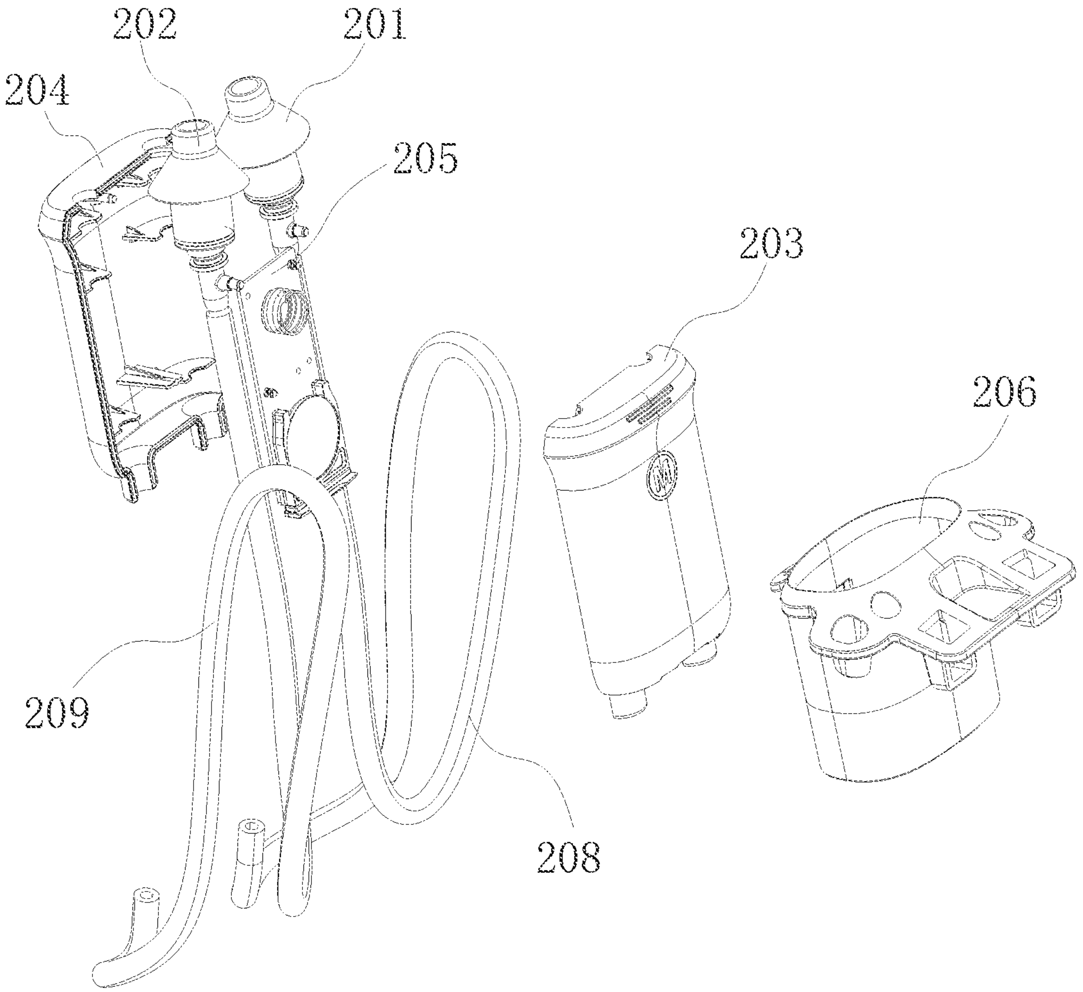
FIG. 4 is an exploded schematic diagram of a nasal irrigator handle according to a first embodiment of the present disclosure.

For the specific structure of the nasal irrigator handle 20, referring to FIG. 4, the present disclosure provides a specific embodiment. The nasal irrigator handle 20 includes handle upper cover 203 and lower handle cover 204 buckled with each other, and a tail end of the water inlet soft rubber nozzle 201 and a tail end of the water return soft rubber nozzle 202 are fixedly clamped between the upper handle cover 203 and the lower handle cover 204. Control printed circuit board (PCB) 205 is provided between the upper handle cover 203 and the lower handle cover 204, and a control button is provided on the upper handle cover 203, and configured to implement control over the water inlet pump 104 and the dirty water pump. In addition, handle cover 206 is provided at the insertion hole of the nasal irrigator body 10, and the nasal irrigator handle 20 is inserted into the handle cover 206. Guide plate 207 is fixedly arranged on a side of the handle cover 206 and is located between the handle cover 206 and the water inlet pump and the dirty water pump 105 arranged side by side. The guide plate 207 can achieve a guide effect when the nasal irrigator handle 20 is inserted in.

For a pipe connection structure, first water inlet pipe 208 is connected to the water inlet soft rubber nozzle 201, and the water inlet soft rubber nozzle 201 is communicated with the water inlet pump 104 through the first water inlet pipe 208; and first water outlet pipe 209 is connected to the water return soft rubber nozzle 202, and the water return soft rubber nozzle 202 is communicated with the dirty water pump 105 through the first water outlet pipe 209. Moreover, a second water inlet pipe (not shown in the figures) is connected to the clean water tank 30, and the clean water tank 30 is communicated with the water inlet pump 104 through the second water inlet pipe; and a second water outlet pipe (not shown in the figures) is connected to the dirty water tank 40, and the dirty water tank 40 is communicated with the dirty water pump 105 through the second water outlet pipe. In addition, as shown in FIG. 7, fixed frame 106 is fixedly arranged in the nasal irrigator body 10, a limiting hole is formed in the fixed frame 106 in a penetrating manner, and the first water inlet pipe 208 and the first water outlet pipe 209 pass through the limiting hole.

Figure 5:
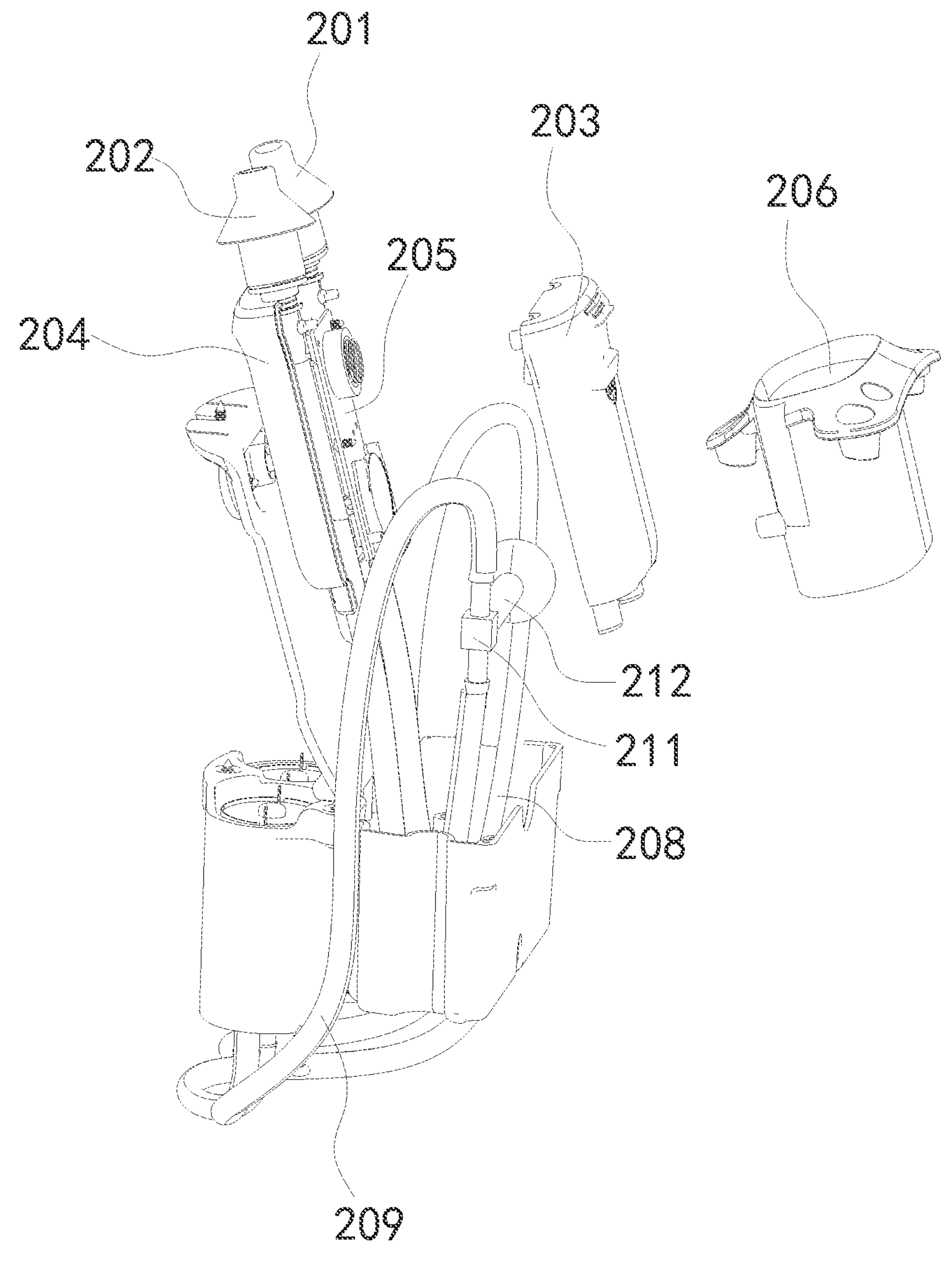
FIG. 5 and FIG. 6 are exploded schematic diagrams of a nasal irrigator handle according to a second embodiment of the present disclosure.

Referring to FIG. 5 and FIG. 6, the present disclosure provides another specific embodiment for the nasal irrigator handle 20. In this embodiment, the structure of the water inlet soft rubber nozzle 201, the structure of the water return soft rubber nozzle 202, the structure of the upper handle cover 203, and the structure of the lower handle cover 204 are all the same as those in the embodiment shown in FIG. 4. The differences are as follows: tee joint 211 is provided at a middle of the first water inlet pipe 208, communication of the first water inlet pipe 208 is implemented by two ends of the tee joint 211, a vent pipe is connected to another port of the tee joint, and air one-way valve 212 is provided at a tail end of the vent pipe and allows injection of air into the first water inlet pipe 208. When starting up, only the dirty water pump works for about 4 seconds (during which the water inlet pump does not work). During this period, only air but no liquid passes through the nose. After about 4 seconds, the dirty water pump and the water inlet pump work normally at the same time. This design helps to improve the comfort of use by opening a nasal membrane at the beginning of ventilation.

Still referring to FIG. 7, the water inlet pump 104 and the dirty water pump 105 are fixed in water pump silicone case 107, body cover 108 is provided on a side of the water pump silicone case 107 and has an accommodating cavity with an open upper end, and a drooping part of the first water inlet pipe 208 and a drooping part of the first water outlet pipe 209 are located in the accommodating cavity of the body cover 108. Therefore, the body cover 108 implements accommodation of the first water inlet pipe 208 and the first water outlet pipe 209, thereby preventing the first water inlet pipe 208 and the first water outlet pipe 209 from being collided with or wound on other parts when the nasal irrigator handle 20 is drawn out, to conveniently take out and place in the nasal irrigator.

Figure 8:
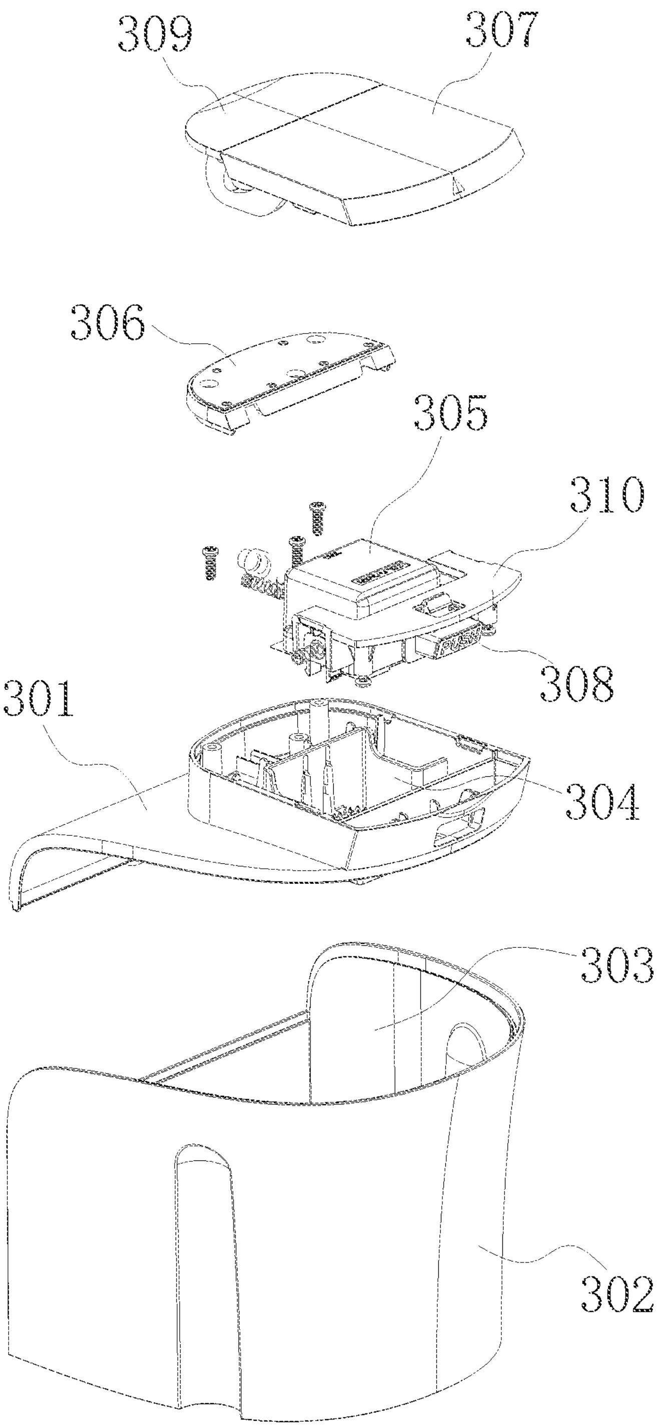
FIG. 8 is an exploded schematic diagram of a clean water tank according to the present disclosure.
Figure 9:
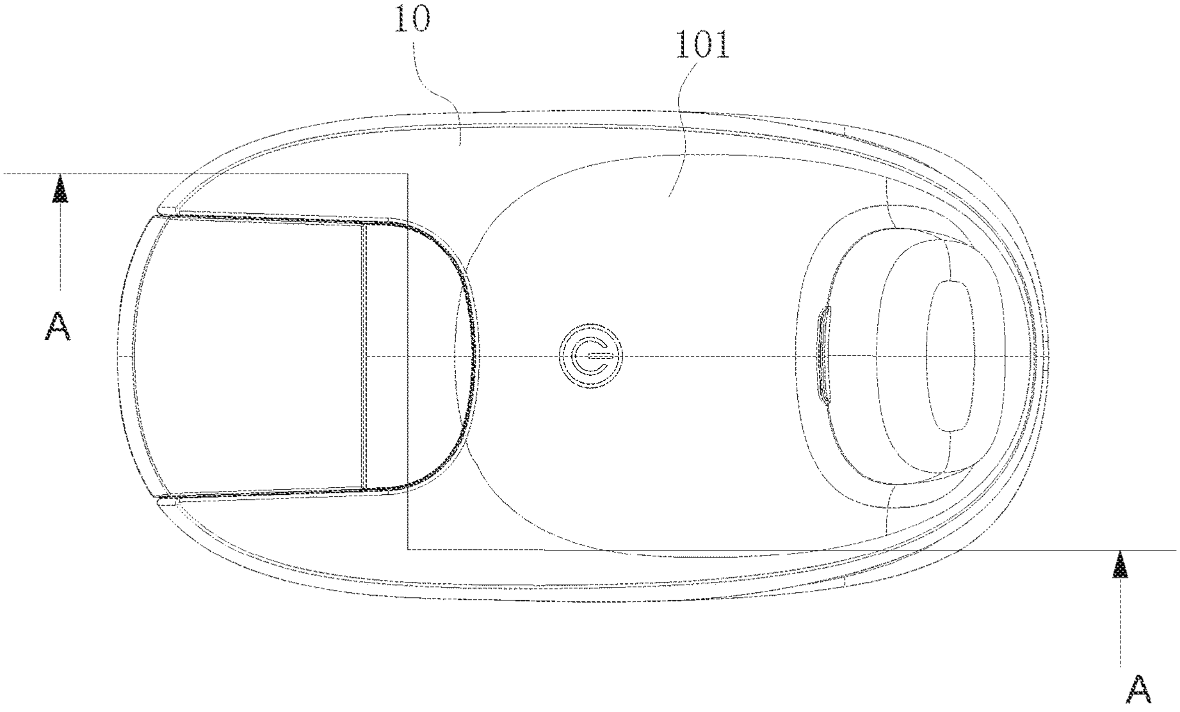
FIG. 9 is a top view of a nasal irrigator according to the present disclosure.
Figure 10:
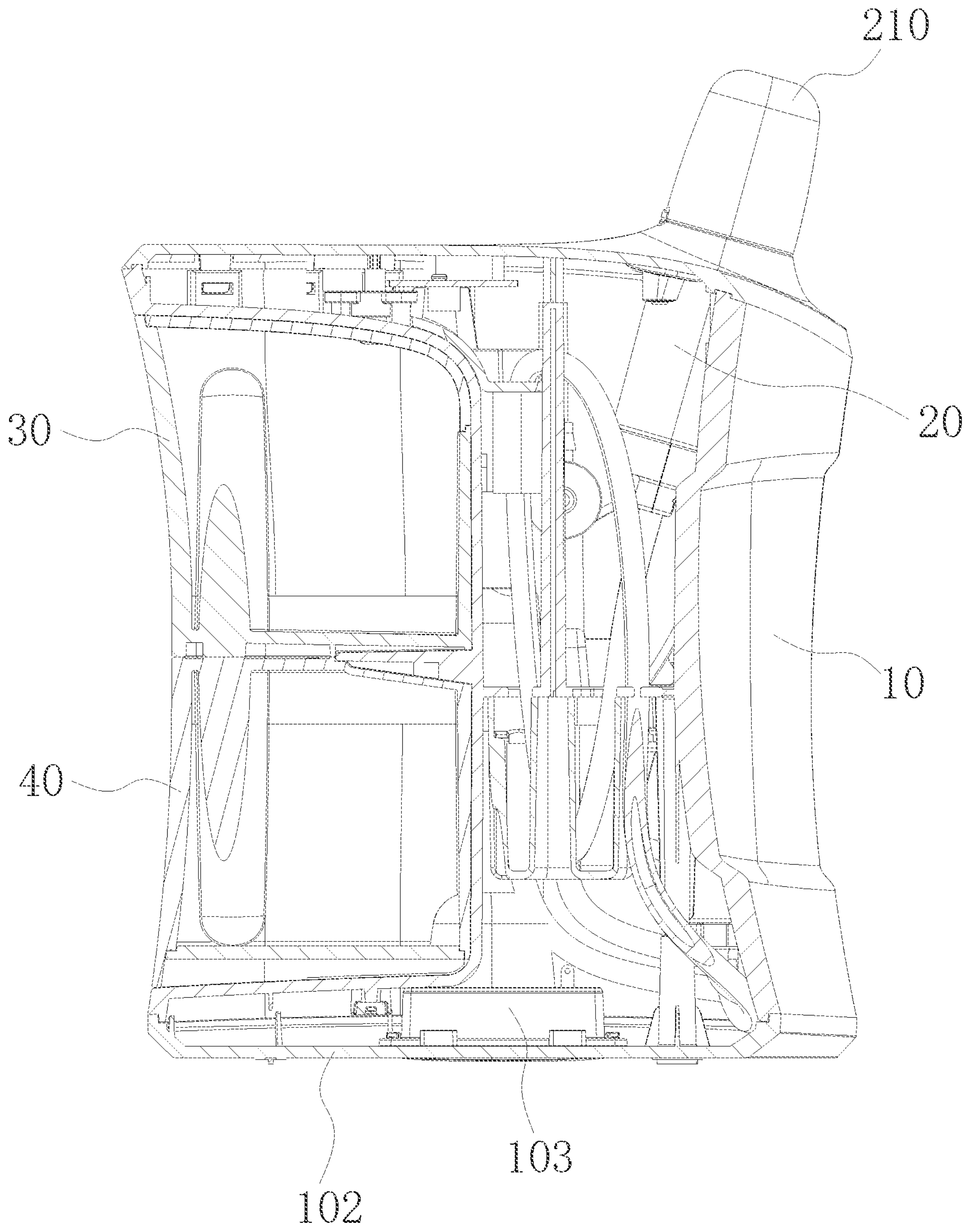
FIG. 10 is a schematic cross-sectional diagram of a place A-A in FIG. 9.

As shown in FIG. 8, for the clean water tank 30, the present disclosure provides a specific embodiment. The clean water tank 30 includes clean water tank upper cover 301 and lower clean water tank cover 302 buckled with the upper clean water tank cover 301, the lower clean water tank cover 302 is provided with first accommodating cavity 303 configured to accommodate clean water, and the first accommodating cavity 303 has a water outlet communicated with the second water inlet pipe.

Still referring to FIG. 8, the upper clean water tank cover 301 is provided with second accommodating cavity 304 configured to accommodate saline pack 305, a through hole communicated with the first accommodating cavity 303 is formed in a bottom surface of the second accommodating cavity 304, and spikes configured to puncture the saline pack are provided on a periphery of the through hole. Through this structure, saline in the saline pack can smoothly enter the first accommodating cavity 303, is mixed with the clean water in the first accommodating cavity 303, and is provided for the user to use. In addition, a magnetic element configured to sense whether the saline pack is placed in is further provided in the second accommodating cavity 304. In this embodiment, the magnetic element is a permanent magnet, and the position of the permanent magnet can be changed after the saline pack is placed in. At a circuit design part, a Hall element is provided on a main control board, and can sense the change of a magnetic field of the permanent magnet to determine whether the saline pack is placed in.

In addition, pressing plate 306 of the upper clean water tank cover and clean water tank clamshell cover 307 are provided in the second accommodating cavity 304, the clean water tank clamshell cover 307 is rotatably connected to the upper clean water tank cover 301, clean water tank button 308 is further provided on the upper clean water tank cover 301, clean water tank elastic cover 310 is further provided in the second accommodating cavity 304, and the clean water tank clamshell cover 307 is open or closed through the clean water tank button 308. Pressing plate outer cover 309 is provided on the pressing plate 306 of the upper clean water tank cover, and the pressing plate outer cover 309 and the clean water tank clamshell cover 307 are located on a same horizontal plane to improve the product aesthetic.

Figure 11:
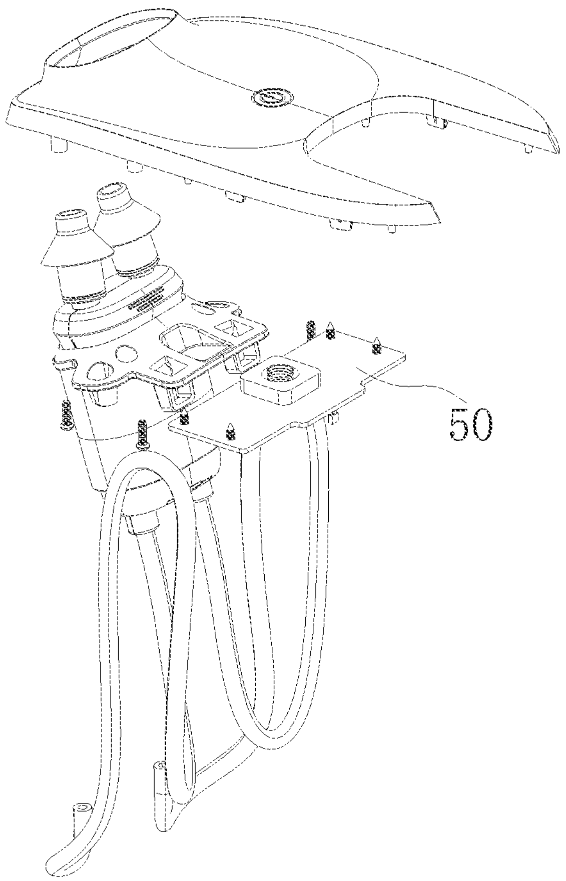
FIG. 11 is a schematic structural diagram of a top cover, a nasal irrigator handle, and a main control PCB according to the present disclosure.

As shown in FIG. 11, control PCB 50 is provided inside the nasal irrigator body 10. As shown in FIG. 12 to FIG. 18, a control circuit is integrated on the control PCB, and the control circuit includes a power supply circuit, a data processing circuit, a water pump control circuit, a bluetooth chip circuit, and a touch detection circuit.

Figure 12:
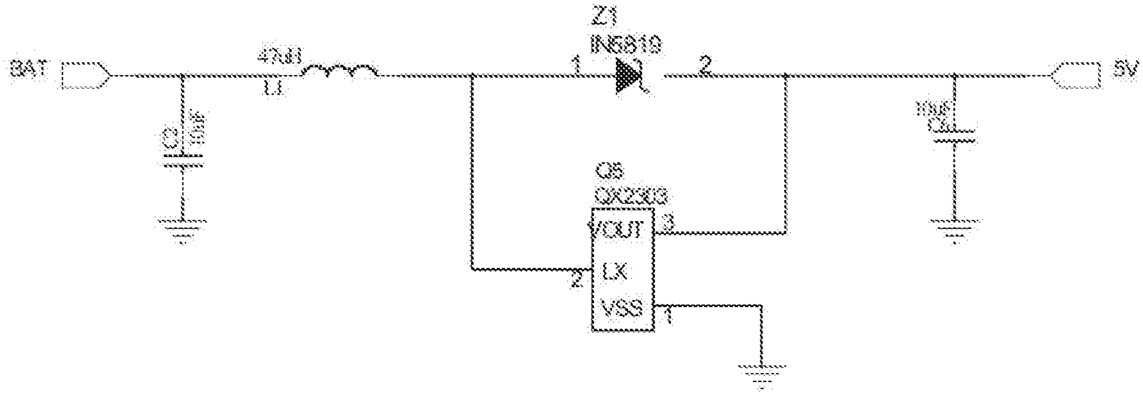
FIG. 12 is a circuit diagram of a first power supply circuit according to the present disclosure.
Figure 13:
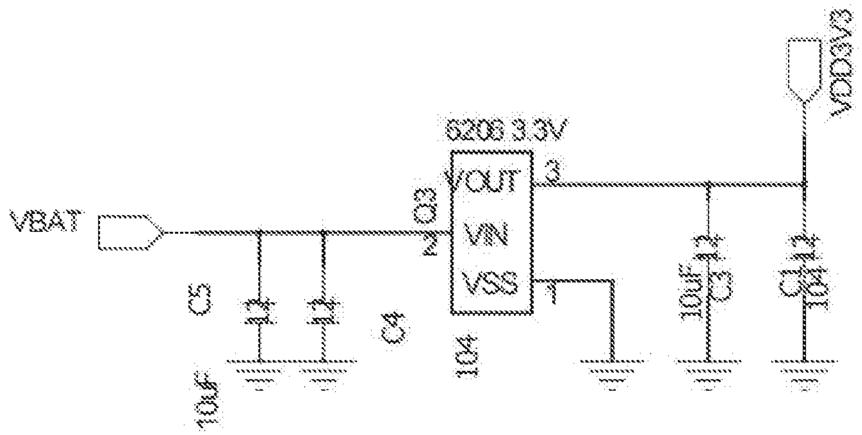
FIG. 13 is a circuit diagram of a second power supply circuit according to the present disclosure.

In this embodiment, the power supply circuit is configured to provide electric energy to other circuits. In this embodiment, the power supply circuit includes a first power supply circuit configured to provide a voltage of direct current 5 V, and a second power supply circuit configured to provide a voltage of direct current 3.3 V FIG. 12 is a circuit diagram of a first power supply circuit, which includes a chip Q5 and a diode Z1. The model of the chip Q5 is QX2303, and the model of the diode Z1 is IN5819. FIG. 13 is a circuit diagram of a second power supply circuit, which includes a chip Q3 having the same structure as the chip Q5.

In this embodiment, the water pump control circuit, the bluetooth chip circuit, and the touch detection circuit are all electrically connected to the data processing circuit and are all controlled by the data processing circuit, and the water pump control circuit is configured to control the water inlet pump 104 and the dirty water pump 105. In addition, the control circuit further includes an antenna circuit electrically connected to the data processing circuit and the touch detection circuit.

Figure 14:
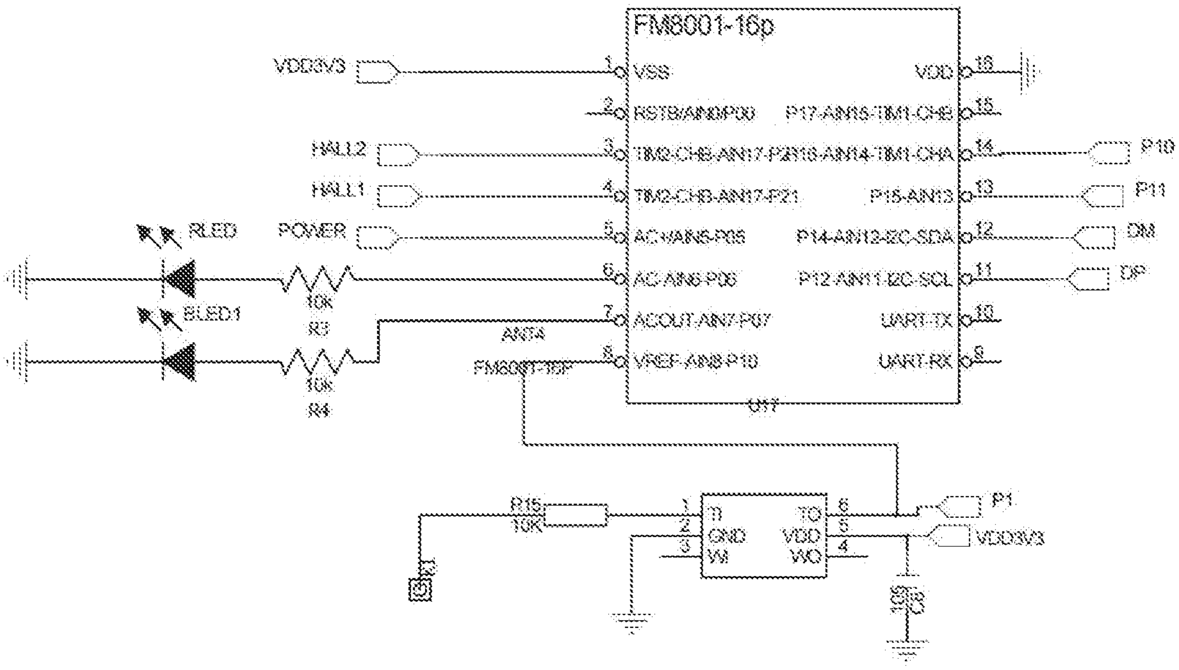
FIG. 14 is a circuit diagram of a data processing circuit according to the present disclosure.
Figure 15:
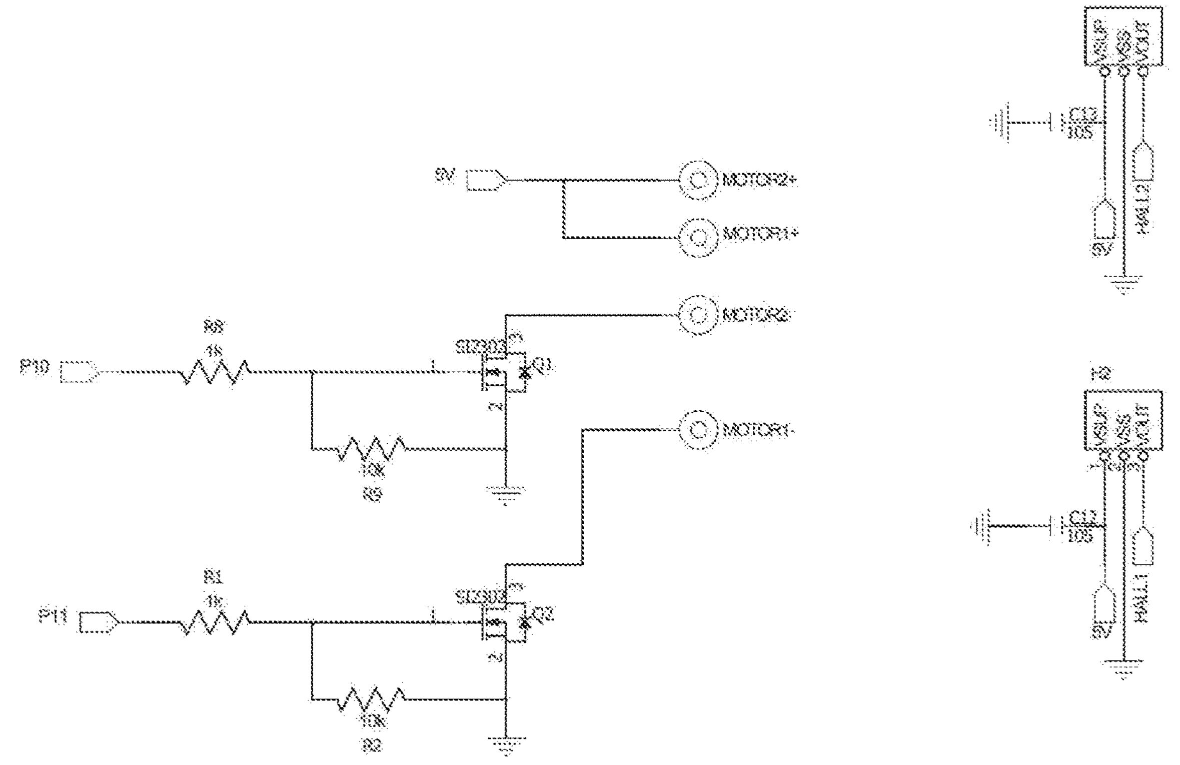
FIG. 15 is a circuit diagram of a water pump control circuit according to the present disclosure.
Figure 16:
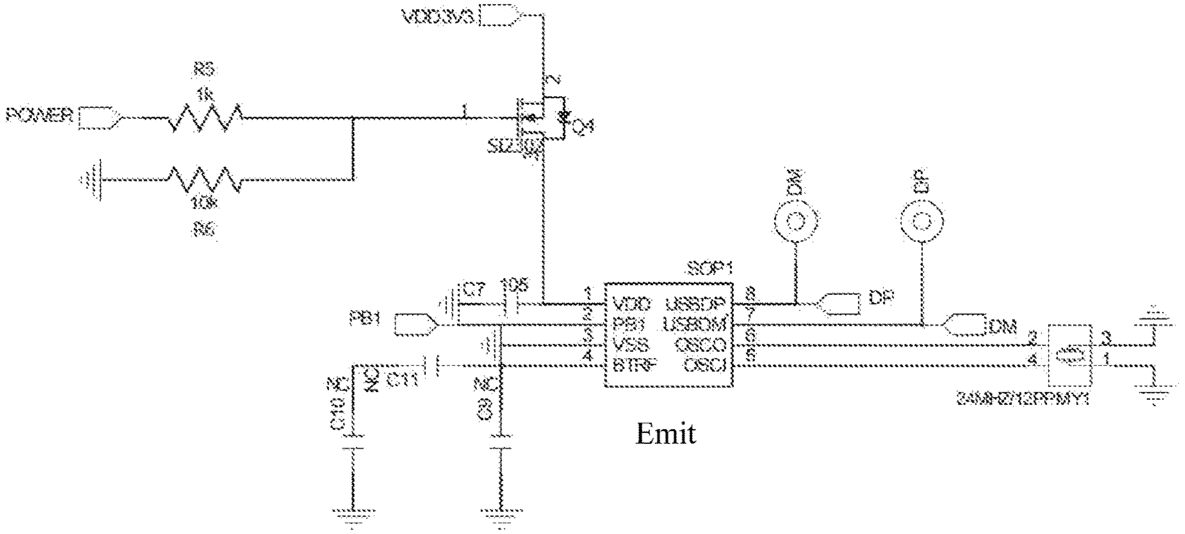
FIG. 16 is a circuit diagram of a bluetooth chip circuit according to the present disclosure.
Figure 17:
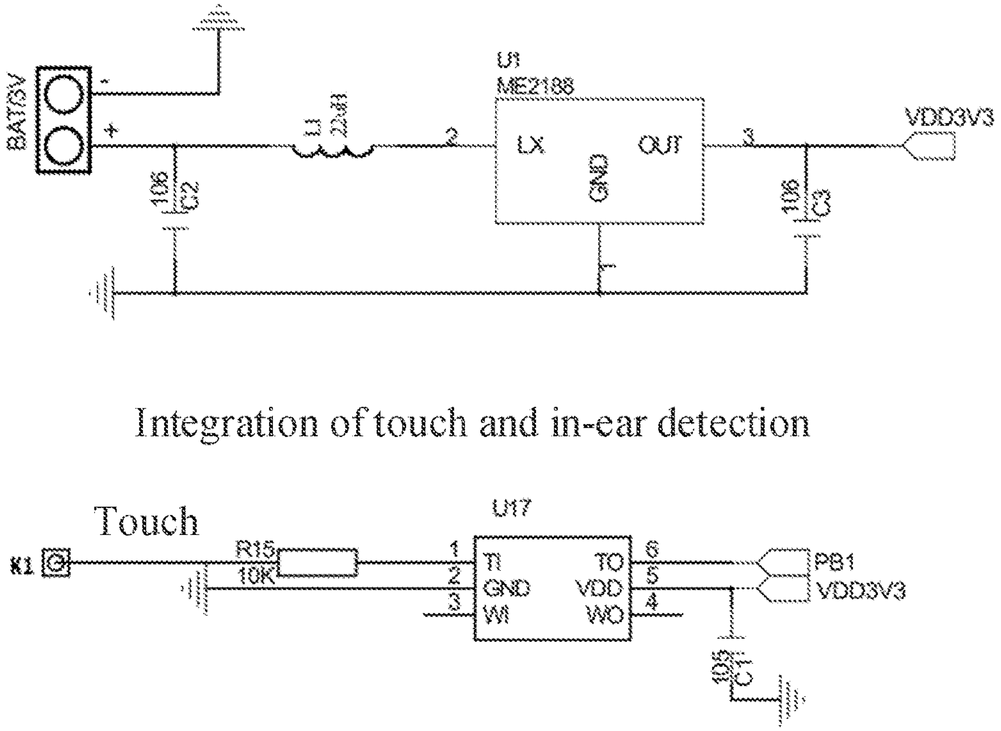
FIG. 17 is a circuit diagram of a touch detection circuit according to the present disclosure.
Figure 18:
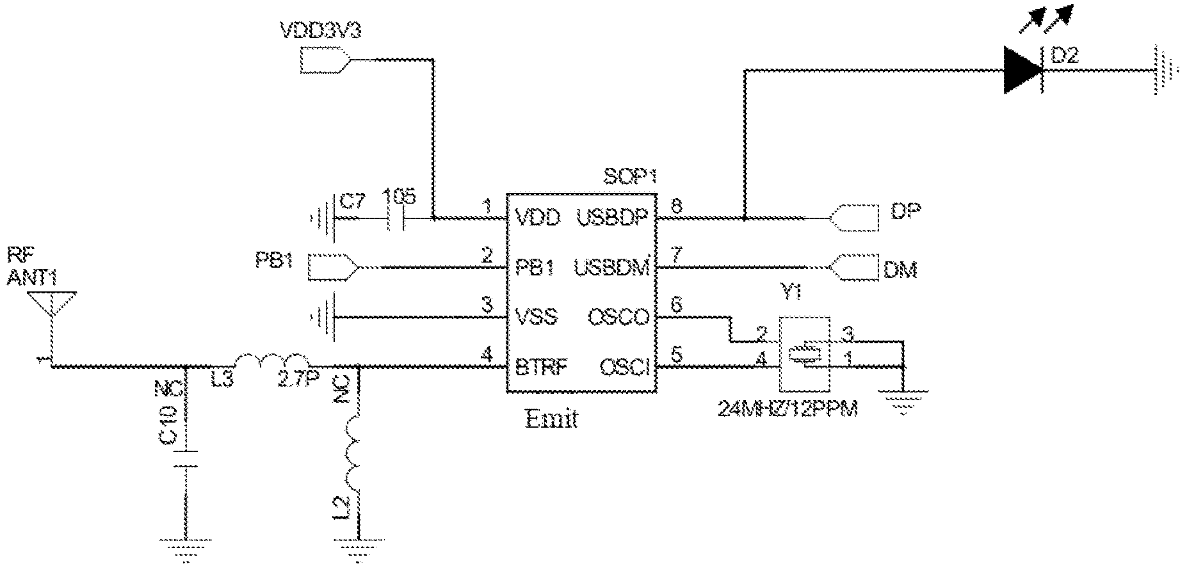
FIG. 18 is a circuit diagram of an antenna circuit according to the present disclosure.

For the specific circuit structure, the present disclosure provides a specific embodiment. FIG. 14 is a circuit diagram of a data processing circuit, which includes a chip U17. The chip U17 has a model of Fm8001-16p, has a logic determination capability, and emits a control instruction according to a received signal. FIG. 15 is a circuit diagram of a water pump control circuit, which includes a metal oxide semiconductor (MOS) transistor Q1 and a MOS transistor Q2. The model of the MOS transistor Q1 and the model of the MOS transistor Q2 are both SI2302. FIG. 16 is a circuit diagram of a bluetooth chip circuit, which includes a bluetooth chip SOP1 and a MOS transistor Q4. The model of the MOS transistor Q4 is SI2302. FIG. 17 is a circuit diagram of a touch detection circuit, which includes a chip UL. The specific model of the chip U1 is ME2188. FIG. 18 is a circuit diagram of an antenna circuit, which includes a chip SOP1, a diode D2, and an antenna ANT1. The antenna circuit implements sending of a wireless signal.

After the battery supplies power, and after the voltage is stabilized by the chip Q5, a direct current of 5 V is outputted to power the water inlet pump 104 and the dirty water pump. At the same time, the other group outputs a direct current of 3.3V to the chip SOP1 for work after the voltage is stabilized by the chip U1. After a corresponding working instruction is received, the working instruction is submitted to the chip U17 for processing, and a software program working instruction is executed to control the working state of the water inlet pump and the working state of the dirty water pump.

The above described are only preferred embodiments of the present disclosure, and the above-mentioned specific embodiments are not intended to limit the present disclosure. Various variations and modifications may be made within the scope of the technical idea of the present disclosure. However, any retouch, modification or equivalent replacement made by those of ordinary skill in the art according to the above description should fall within the protection scope of the present disclosure.

What is claimed is:

1. A nasal irrigator, comprising a nasal irrigator body, a nasal irrigator handle, a clean water tank, and a dirty water tank, wherein the clean water tank and the dirty water tank are arranged on a side of the nasal irrigator body, and a water inlet pump communicated with the clean water tank and a dirty water pump communicated with the dirty water tank are provided inside the nasal irrigator body;

the nasal irrigator body is provided with an insertion hole configured to fix the nasal irrigator handle, and the nasal irrigator handle is allowed to be inserted into the insertion hole or taken out of the insertion hole; and a water inlet soft rubber nozzle and a water return soft rubber nozzle are mounted on the nasal irrigator handle, the water inlet soft rubber nozzle is communicated with the water inlet pump, and the water return soft rubber nozzle is communicated with the dirty water pump;

a first water inlet pipe is connected to the water inlet soft rubber nozzle, and the water inlet soft rubber nozzle is communicated with the water inlet pump through the first water inlet pipe; and a first water outlet pipe is connected to the water return soft rubber nozzle, and the water return soft rubber nozzle is communicated with the dirty water pump through the first water outlet pipe; and the water inlet pump and the dirty water pump are fixed in a water pump silicone case, a body cover is provided on a side of the water pump silicone case and has an accommodating cavity with an open upper end, and a drooping part of the first water inlet pipe and a drooping part of the first water outlet pipe are located in the accommodating cavity of the body cover.

2. The nasal irrigator according to claim 1, wherein the nasal irrigator handle comprises an upper handle cover and a lower handle cover buckled with each other, and a tail end of the water inlet soft rubber nozzle and a tail end of the water return soft rubber nozzle are fixedly clamped between the upper handle cover and the lower handle cover.

3. The nasal irrigator according to claim 2, wherein a control printed circuit board (PCB) is provided between the upper handle cover and the lower handle cover, a control button is provided on the upper handle cover, and configured to implement control over the water inlet pump and the dirty water pump.

4. The nasal irrigator according to claim 2, wherein a handle cover is provided at the insertion hole of the nasal irrigator body, and the nasal irrigator handle is inserted into the handle cover; and a guide plate is fixedly arranged on a side of the handle cover and is located between the handle cover and the water inlet pump and the dirty water pump arranged side by side.

5. The nasal irrigator according to claim 1, wherein a second water inlet pipe is connected to the clean water tank, and the clean water tank is communicated with the water inlet pump through the second water inlet pipe; and a second water outlet pipe is connected to the dirty water tank, and the dirty water tank is communicated with the dirty water pump through the second water outlet pipe.

6. The nasal irrigator according to claim 1, wherein a fixed frame is fixedly arranged in the nasal irrigator body, a limiting hole is formed in the fixed frame in a penetrating manner, and the first water inlet pipe and the first water outlet pipe pass through the limiting hole.

7. The nasal irrigator according to claim 1, wherein a tee joint is provided at a middle of the first water inlet pipe, communication of the first water inlet pipe is implemented by two ends of the tee joint, a vent pipe is connected to another port of the tee joint, and an air one-way valve is provided at a tail end of the vent pipe and allows injection of air into the first water inlet pipe.

8. The nasal irrigator according to claim 1, wherein the clean water tank comprises an upper clean water tank cover and a lower clean water tank cover buckled with the upper clean water tank cover, and the lower clean water tank cover is provided with a first accommodating cavity configured to accommodate clean water.

9. A nasal irrigator, comprising a nasal irrigator body, a nasal irrigator handle, a clean water tank, and a dirty water tank, wherein the clean water tank and the dirty water tank are arranged on a side of the nasal irrigator body, and a water inlet pump communicated with the clean water tank and a dirty water pump communicated with the dirty water tank are provided inside the nasal irrigator body;

the nasal irrigator body is provided with an insertion hole configured to fix the nasal irrigator handle, and the nasal irrigator handle is allowed to be inserted into the insertion hole or taken out of the insertion hole; and a water inlet soft rubber nozzle and a water return soft rubber nozzle are mounted on the nasal irrigator handle, the water inlet soft rubber nozzle is communicated with the water inlet pump, and the water return soft rubber nozzle is communicated with the dirty water pump;

the clean water tank comprises an upper clean water tank cover and a lower clean water tank cover buckled with the upper clean water tank cover, and the lower clean water tank cover is provided with a first accommodating cavity configured to accommodate clean water; and the upper clean water tank cover is provided with a second accommodating cavity configured to accommodate a saline pack, a through hole communicated with the first accommodating cavity is formed in a bottom surface of the second accommodating cavity, and spikes configured to puncture the saline pack are provided on a periphery of the through hole.

10. The nasal irrigator according to claim 9, wherein a pressing plate of the upper clean water tank cover and a clean water tank clamshell cover are provided in the second accommodating cavity, the clean water tank clamshell cover is rotatably connected to the upper clean water tank cover, a clean water tank button is further provided on the upper clean water tank cover, and the clean water tank clamshell cover is open or closed through the clean water tank button.

11. The nasal irrigator according to claim 9, wherein a magnetic element is further provided in the second accommodating cavity of the upper clean water tank cover, wherein the magnetic element is configured to sense whether the saline pack is placed in.

12. The nasal irrigator according to claim 1, wherein a notch recessed inward is formed in the side of the nasal irrigator body, and the clean water tank and the dirty water tank are arranged side by side along a vertical direction and then are disposed in the notch of the nasal irrigator body.

13. The nasal irrigator according to claim 1, wherein a top cover is provided at a top of the nasal irrigator body, a bottom cover is provided at a bottom of the nasal irrigator body, and a battery box configured to accommodate a battery is provided on the bottom cover.

14. The nasal irrigator according to claim 1, wherein a control PCB is provided inside the nasal irrigator body, a control circuit is integrated on the control PCB, and the control circuit comprises a power supply circuit, a data processing circuit, a water pump control circuit, a bluetooth chip circuit, and a touch detection circuit, wherein the power supply circuit is configured to provide electric energy to the data processing circuit, the water pump control circuit, the bluetooth chip circuit, and the touch detection circuit; and the water pump control circuit, the bluetooth chip circuit, and the touch detection circuit are electrically connected to the data processing circuit and are controlled by the data processing circuit, and the water pump control circuit is configured to control the water inlet pump and the dirty water pump.

15. The nasal irrigator according to claim 14, wherein the control circuit further comprises an antenna circuit, and the antenna circuit is electrically connected to the data processing circuit and the touch detection circuit.

16. The nasal irrigator according to claim 14, wherein the power supply circuit comprises a first power supply circuit and a second power supply circuit, wherein the first power supply circuit is configured to provide a voltage of direct current 5 V, and the second power supply circuit is configured to provide a voltage of direct current 3.3 V.

* * * * *